United States Patent
Salyer

(10) Patent No.: US 6,428,543 B1
(45) Date of Patent: *Aug. 6, 2002

(54) ACETABULAR REAMER CUP AND METHOD OF PRODUCING THE SAME

(75) Inventor: Paul E. Salyer, Warsaw, IN (US)

(73) Assignee: Othy, Inc., Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/374,034

(22) Filed: Aug. 13, 1999

Related U.S. Application Data

(62) Division of application No. 09/008,723, filed on Jan. 19, 1998, now Pat. No. 6,001,105, which is a division of application No. 08/473,371, filed on Jun. 7, 1995, now Pat. No. 5,709,688.

(51) Int. Cl.$^7$ ............................................... A61B 17/00
(52) U.S. Cl. ....................................................... 606/81
(58) Field of Search .............................. 606/81, 86, 90, 606/91; 623/22; 30/276; 408/204, 703, 226, 205

(56) References Cited

U.S. PATENT DOCUMENTS

| | | | |
|---|---|---|---|
| 2,785,673 A | | 3/1957 | Anderson |
| 3,633,583 A | | 1/1972 | Fishbein |
| 3,667,456 A | | 6/1972 | Charnley |
| 3,702,611 A | | 11/1972 | Fishbein |
| 4,023,572 A | | 5/1977 | Weigand et al. |
| 4,072,441 A | | 2/1978 | LaPointe |
| 4,116,200 A | | 9/1978 | Braun et al. |
| 4,131,116 A | | 12/1978 | Hedrick |
| 4,811,632 A | * | 3/1989 | Salyer ........................ 606/81 |
| 5,100,267 A | | 3/1992 | Salyer |
| 5,116,165 A | | 5/1992 | Salyer |
| 5,236,433 A | | 8/1993 | Salyer |
| 5,299,893 A | | 4/1994 | Salyer et al. |
| 5,709,688 A | * | 1/1998 | Salyer ........................ 606/81 |

FOREIGN PATENT DOCUMENTS

| | | |
|---|---|---|
| DE | 2500958 | 11/1975 |
| GB | 666621 | 2/1952 |
| SU | 166449 | 3/1965 |

* cited by examiner

Primary Examiner—David O. Reip
Assistant Examiner—Tan-Uyen T. Ho
(74) Attorney, Agent, or Firm—Taylor & Aust, P.C.

(57) ABSTRACT

A method for making an acetabular reamer for an acetabular reamer comprising the steps of: fabricating a bowl shaped cup-blank having outer and inner bowl shaped surfaces, perforating a plurality of holes through the cup-blank, the holes each are surrounded by a curved margin, deforming outwardly of the outer surface a cutting portion of the margin of each of the holes, thereby forming cutting edges, the cutting portions are curved outwardly of the outer surface, the cutting edges are curved tangentially of the outer surface and disposed to cut upon rotation of the acetabular reamer.

An acetabular reamer cup is also provided comprising a cutting bowl having a plurality of curved cutting edges, the cutting bowl has a plurality of openings preceding the cutting edges, the cutting bowl has a generally conical rise following the cutting edges, the cutting edges are spirally arranged about the axis of rotation of the cutting bowl, and a bottom adjoined to the cutting bowl, the bottom has a tool driver opening coaxial with the cutting bowl and the cutting edges.

16 Claims, 2 Drawing Sheets

ACETABULAR REAMER CUP AND METHOD OF PRODUCING THE SAME

This application is a divisional of U.S. patent application Ser. No. 08/473,371 filed on Jun. 7, 1995, entitled "Acetabular Reamer Cup and Method of Producing the Same" by the same inventor now U.S. Pat. No. 5,709,688 and is a sister application of U.S. patent application Ser. No. 09/008,723 filed on Jan. 19, 1998 entitled "Acetabular Reamer Cup and Method of Producing the Same" by the same inventor is now U.S. Pat. No. 6,001,105 which is also a divisional application of U.S. patent application Ser. No. 08/473,371.

BACKGROUND OF THE INVENTION

The present invention pertains to acetabular reamers, and more particularly, to acetabular reamer cups.

Acetabular reamers are used by surgeons to prepare pelvic bones and the like for insertion of artificial joints. An acetabular reamer is rotated to cut a cavity into the bone into which the socket portion of the artificial joint can be inserted. Dimensions and shape of the cavity cut are critical as the tolerances between the cavity and the socket portion of a joint must be small to insure proper function. This is especially true with the newly available "cementless" hip joints. Before "cementless" hip joints, the socket portion of the joint was cemented into the cavity. In the "cementless" joint, the socket portion is frictionally fit into the cavity, placing new importance upon accurate cavity dimensions and tolerances.

In the past methods of making acetabular reamer cups, holes in the cup were countersunk from the inside and then a part of the edge of the hole was pushed up and subsequently hand sharpened. This process is slow and very dependent upon the skill of the individual workman sharpening the edges. The acetabular reamer cup produced by that method has edges sharpened to a double bevel and as a result, the edges stay sharp only a relatively short period of time. Another method of producing an acetabular reamer is disclosed in U.S. Pat. No. 4,811,632 in which holes in the cup are deformed outwardly of the exterior surface to provide a cutting portion of the hole margin, smoothing the outer surface of the cup to sharpen the cutting portions, and subsequently raising the curved cutting edges from the cutting portions outwardly of the surface. This method provides an acetabular reamer cup that has edges sharpened to a single bevel and as result the edges stay sharper than the prior described method, but the method includes multiple steps, and the deforming and smoothing steps do not produce an acetabular reamer cup with uniform cutting edges or exceedingly tight dimensions and/or tolerances.

Additionally, in utilizing prior acetabular reamer cups, surgeons have experienced slow cutting speeds, a requirement of considerable strength to force the reamer cup against the bone to be cut, and thermal osteonecrosis all of which should be minimized or eliminated.

It is therefore highly desirable to provide an improved acetabular reamer cup and method for making the same.

It is also highly desirable to provide an improved acetabular reamer cup which is capable of more accurate cavity dimensions and smaller tolerances, and an improved method for making the same.

It is also highly desirable to provide an improved acetabular reamer cup which minimizes thermal osteonecrosis and an improved method for making the same.

It is also highly desirable to provide an improved acetabular reamer cup which cuts faster and requires less force against the bone than prior acetabular reamer cups, and an improved method for making the same.

It is also highly desirable to provide an improved method for making acetabular reamer cups which has less productions steps than prior methods.

It is also highly desirable to provide an improved method for producing an acetabular reamer cup that is faster cutting and more economical to manufacture than past methods and which provides a cup which has improved tolerances and improved cutting edges.

Finally, it is highly desirable to provide an improved acetabular reamer cup and method for making the same which possess all of the above desired features.

SUMMARY OF THE INVENTION

It is therefore an object of the invention to provide an improved acetabular reamer cup and method for making the same.

It is also an object of the invention to provide an improved acetabular reamer cup which is capable of more accurate cavity dimensions and smaller tolerances, and an improved method for making the same.

It is also an object of the invention to provide an improved acetabular reamer cup which minimizes thermal osteonecrosis and an improved method for making the same.

It is also an object of the invention to provide an improved acetabular reamer cup which cuts faster and requires less force against the bone than prior acetabular reamer cups, and an improved method for making the same.

It is also an object of the invention to provide an improved method for making acetabular reamer cups which has less productions steps than prior methods.

It is also an object of the invention to provide an improved method for producing an acetabular reamer cup that is faster cutting and more economical to manufacture than past methods and which provides a cup which has improved tolerances and improved cutting edges.

It is finally an object of the invention to provide an improved acetabular reamer cup and method for making the same which possess all of the above desired features.

In the broader aspects of the invention, there is provided a method for making an acetabular reamer for an acetabular reamer comprising the steps of: fabricating a bowl shaped cup-blank having outer and inner bowl shaped surfaces, perforating a plurality of holes through the cup-blank, the holes each are surrounded by a curved margin, deforming outwardly of the outer surface a cutting portion of the margin of each of the holes, thereby forming cutting edges, the cutting portions are curved outwardly of the outer surface, the cutting edges are curved tangentially of the outer surface and disposed to cut upon rotation of the acetabular reamer.

An acetabular reamer cup is also provided comprising a cutting bowl having a plurality of curved cutting edges, the cutting bowl has a plurality of openings preceding the cutting edges, the cutting bowl has a generally conical rise following the cutting edges, the cutting edges are spirally arranged about the axis of rotation of the cutting bowl, and a bottom adjoined to the cutting bowl, the bottom has a tool driver opening coaxial with the cutting bowl and the cutting edges.

BRIEF DESCRIPTION OF THE DRAWINGS

The above-mentioned and other features and objects of the invention and the manner of attaining them will become more apparent and the invention itself will be better understood by reference to the following description of an embodiment of the invention taken in conjunction with the accompanying drawings wherein.

DESCRIPTION OF A SPECIFIC EMBODIMENT

Figure 1:
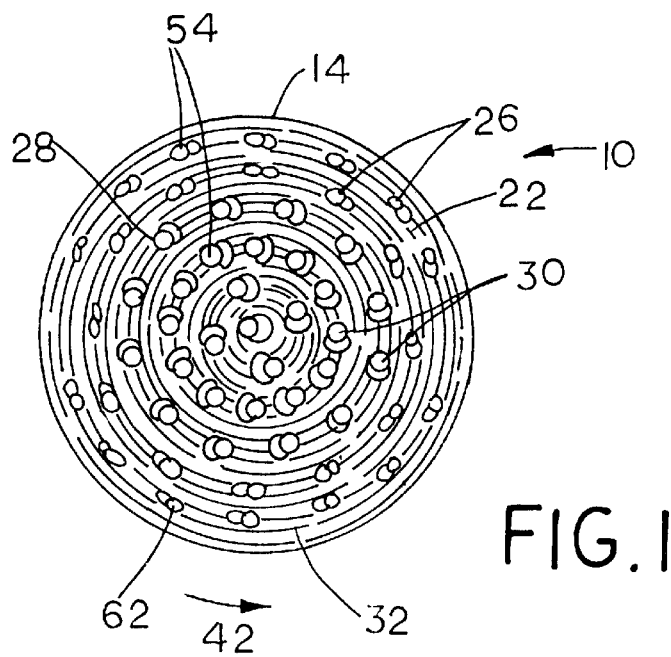
FIG. 1 is a top plan view of the acetabular reamer cup of the invention.
Figure 2:
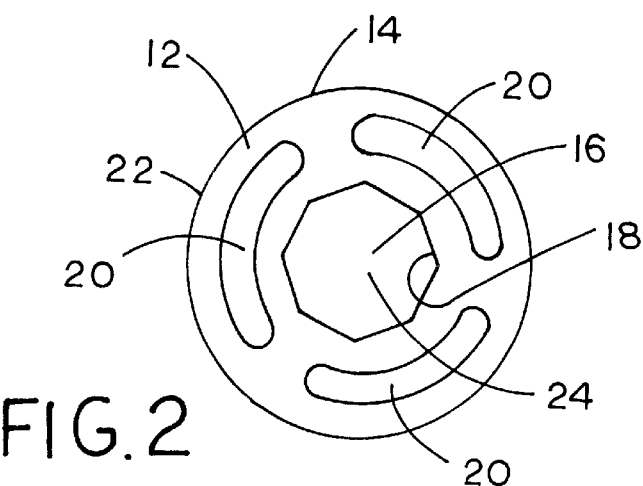
FIG. 2 is a bottom plan view of the acetabular reamer cup of the invention.

The acetabular reamer cup 10 of the invention has a bottom 12 and a cutting bowl 14 which together surround a hollow debris compartment 16. Bottom 12 may be flat or may be angled rearwardly so as to eliminate internal 90° angles which could retain contaminants. Bottom 12 has a tool driver opening 18 which is concentric with the cutting bowl 14. Debris openings 20 may be provided for clearance of debris during use. Cutting bowl 14 has a body portion 22 which is substantially hemispherical in shape and has an axis of rotation 24. Cutting bowl 14 has a spirally arranged pattern of outwardly extending cutters 26 and adjoining openings 28. Each acetabular reamer cup 10 has a particular handedness, that is, a direction of rotation 42 about axis of rotation 24 in which acetabular reamer cup 10 must be rotated in order for the acetabular reamer cup 10 to cut. Each opening 28 precedes a respective cutter 26 that is during the rotation of the acetabular reamer cup 10 about axis of rotation 24. Each opening 28 sweeps an area before a respective cutter 26. With a right handed acetabular cup 10 that cuts when pressed against a substrate and rotated in a clockwise direction, openings 28 are to the right of the respective cutters 26.

The cutting bowl 14 of the acetabular reamer cup 10 in a specific embodiment is generally bowl shaped and in the specific embodiment illustrated hemispherical, however, the invention is not limited to a hemispherical bowl shaped cups 10, but may include bowl shaped cups of other portions of a sphere or cups with the shape of other surfaces of revolution. In other specific embodiments the acetabular reamer cup 10 may be of a material capable of holding a sharpened edge through a reasonable period of use. Stainless steel is one of the materials that is suitable for the acetabular reamer cup 10.

Each cutter 26 has a continuous cutting edge 30 which is doubly curved. Cutting edges 30 have a curvature both in planes perpendicular to the hemispherical surface 32 of the body portion 22 and in planes tangential to the horizontal surface 32 of the body portion 22 and parallel thereto. In other words, each cutting edge 30 is doubly curved. Each cutting edge 30 has opposite ends 34 and 36. Looking at each cutting edge 30 in planes perpendicular to the hemispherical surface 32 of body portion 22 both ends 34 and 36 are more adjacent to the surface 32 than the cutting edge 30 therebetween. Viewing the cutting edge 30 in planes tangential to the surface 32 and in planes parallel thereto, both ends 34 and 36 lead, in the direction of rotation 42, the cutting edge 30 therebetween.

Figure 3:
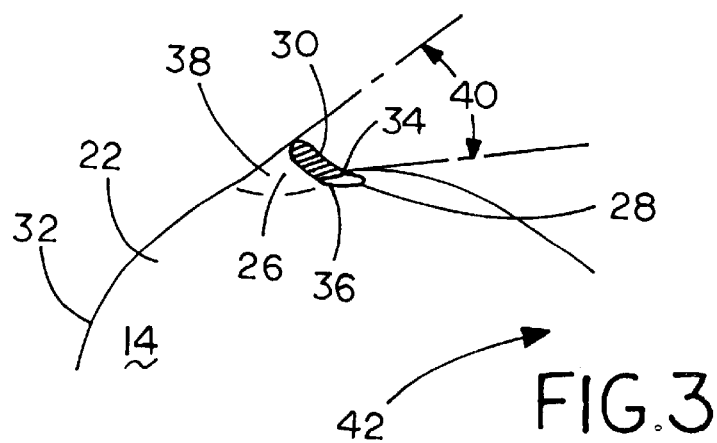
FIG. 3 is an enlarged side view of a cutter of the invention.
Figure 4:
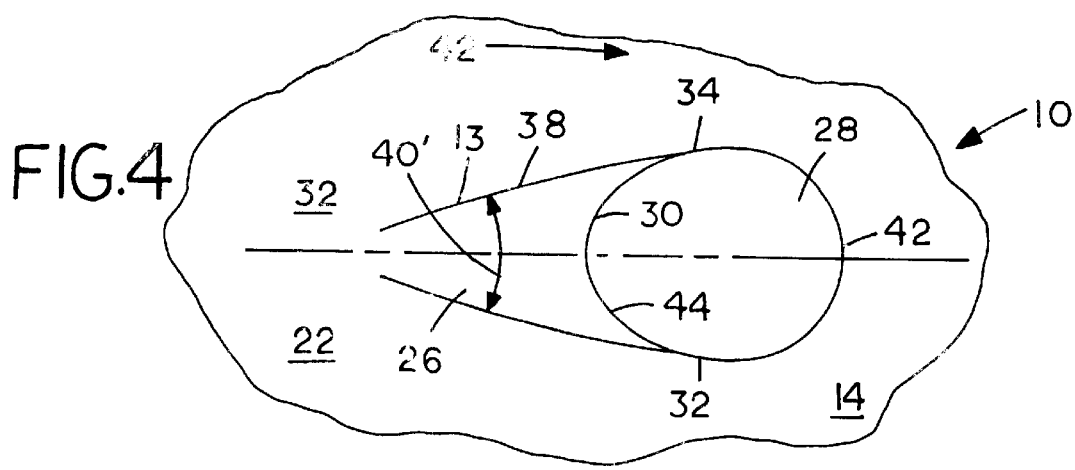
FIG. 4 is an enlarged top view of a cutter of the invention.

Referring to FIGS. 3 and 4, cutting edge 30 is shown backed by a generally conical raised portion 38. Conical portion 38 has an apex angle 40 in planes perpendicular to the exterior surface 32 of the acetabular reamer cup 10 ranging from about 8° to about 46°. In a specific embodiment, the apex angle 40 in planes perpendicular to the exterior surface 32 of the acetabular reamer cup 10 range from about 13° to about 23°. Conical portion 38 has an apex angle 40' which in planes tangential to the exterior surface of acetabular reamer cup 10 and in planes parallel thereto can be measured from about 8° to about 46°. In a specific embodiment, the apex angle 40 in planes tangential to the exterior surface of the acetabular reamer cup 10 and in planes parallel thereto is from about 8° to about 18°. Thus like the generally circular openings 28 preceding the cutting edges 30, neither the openings 28 nor the cones 38 are truly circular and conical, respectively but generally circular and conical. Openings 28 are in fact "egg shaped" having a larger end 42 and a smaller end 44. Smaller end 44 is adjacent cutting edge 30. Larger end 42 is remote from cutting edge 30.

Cutting edge 30 is also angularly disposed to the exterior surface of the acetabular reamer cup 10 as shown in FIGS. 3 and 4. Cutting edge 30 forms with the exterior surface of acetabular reamer cup 10 and obtuse angle ranging from in a specific embodiment, 130° to 140°. Thus it will be seen that each of the cutting edges 30 are always disposed angularly of the direction of rotation of the cutting edges. Thus, the cutting edges cut the bone in shear rather than "head on", so as to cut the bone rather than to chip the bone. This "shear action" of the cutting edges both prolongs the sharpness and therefore the usefulness of the cutting edge, and reduces chipping thereby improving the tolerances which can be accomplished by the acetabular reamer cup 10 of the invention.

Each of the cutting edges 30 follow other cutting edges 30. Each of the cutting edges 30 sweeps an area overlapped by one or more of the other cutting edges 30. In a specific embodiment, the following cutting edges 30 overlap the leading cutting edges 30 a total of about one and one-half times.

In the method of the invention, the acetabular reamer cup 10 of the invention may be manufactured with less steps than heretofore conventional. A bowl shaped cup-blank 48 is first formed of a material capable of holding a sharpened edge through a reasonable period of use. Stainless steel is one of the materials that is suitable for the cup-blank 48.

Figure 6:
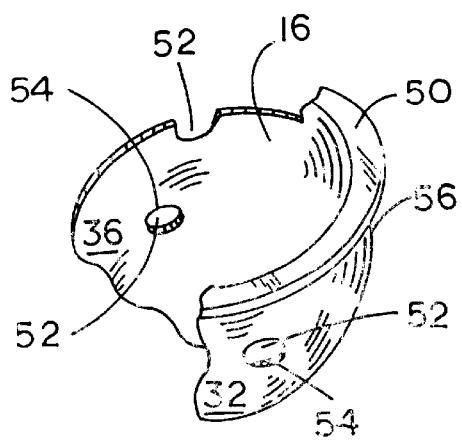
FIG. 6 is a fragmentary cross-sectional view of the perforated cup-blank following the performance of the perforating step of the method of the invention.
Figure 5:
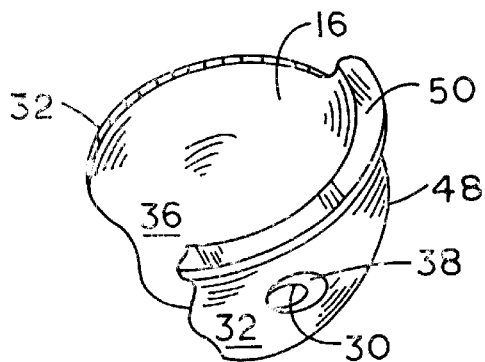
FIG. 5 is a fragmentary cross-sectional view of a cup-blank following the bowl shaped cup-blank fabricating step of the invention.
Figure 7:
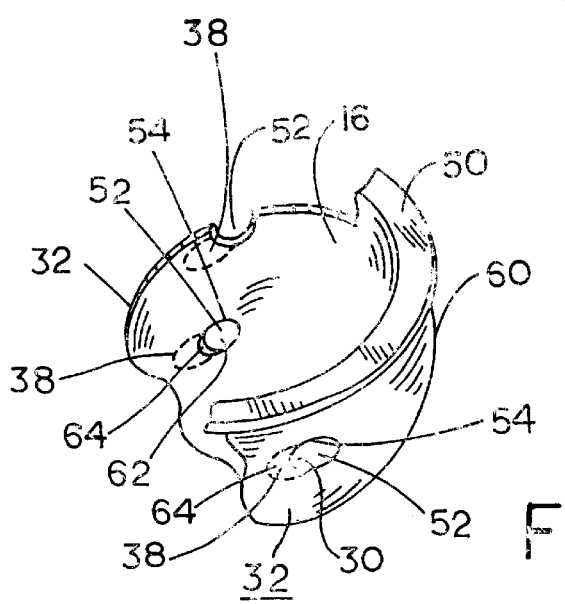
FIG. 7 is a fragmentary cross-sectional view of the acetabular reamer cup of the invention following both the deforming and the sharpening steps of the method of the invention.

In the method of the invention, illustrated in FIGS. 5, 6 and 7, a solid bowl shaped cup-blank 48 is first fabricated. This may be done by drawing or by any equivalent method. In this application, precursors of the acetabular reamer cup 10 will be referred to generally as a cup-blank and specifically as modified forms of that term such as for example "solid cup-blank". In a specific embodiment of the invention the bowl shaped cup-blank 48 includes a peripheral lip 50 which increases the strength of the cup-blank 48 and provides a means by which the cup-blank may be held during the latter steps of fabrication. In this embodiment, the peripheral lip 50 is removed before the acetabular reamer cup 10 is completed.

After the solid cup-blank is fabricated, the solid cup-blank 48 is perforated with the plurality of holes 52 each surrounded by a margin 54. This yields a perforated cup-blank 56. If the holes 52 are formed by a method that produces burs, the perforated cup-blank 56 must be deburred. The holes may be punched or drilled or formed by other equivalent means. It is convenient to make the holes 58 round, however, this method is not limited to round holes. All the holes, however, must be either round or oval or "egg shaped" or, generally a round hole with radiuses of different lengths and different directions. In a specific embodiment of the method of the invention, the holes 52 are cut in a pattern which defines a spiral shape upon rotation of the acetabular reamer cup 10 about its axis. See FIG. 1.

The cutting portion 58 of the margin 54 of each hole 28 is then deformed outwardly to yield a relieved cup-blank 60 and result in a cutting portion 58 which is curved generally in the direction of the surface of the cup-blank with a radius or minor axis of a non-circular arc shorter than the radius or minor axis of the cup-blank 48 as determined by the deformation and curved generally tangentially of the cup-blank surfaces as determined by the curvature of the margin 54 prior to deformation. In a specific embodiment, the cutting portions 58 are each individually deformed outwardly and this is repeated for every opening 28. See FIG. 7.

In a specific embodiment of the invention described herein, cutting portions 58 each extend over a substantial portion of the respective margin 54, but substantially less than the entire margin 54. In specific embodiments of the invention, the cuttings portions 58 extend between 200° and 270° around the openings 28. In a specific embodiment of the invention, cutting portions 58 extend about 240° around the openings 28.

Each of the cutting portions 58 are now sharpened by inserting a rotary "rats tail" grinder within each of the openings 28 to form a bevel 62 and a cutting edge 64 having the requisite sharpness for cutting bone. Each of the bevels 62 of the cutting edges 64 face inwardly of the bowl 14 in contrast to the acetabular reamer cup of U.S. Pat. No. 4,811,632 and are formed generally without the smoothing and raising operations of the method disclosed therein. By this technique, all the cutting edges are similarly raised when the margins 54 are deformed outwardly. In a specific embodiment, this deformation is accomplished by a punching operation which can be accurately controlled to control the tolerances of the cutting edges.

Since there is no further step to alter the tolerances of the cutting edges, i.e. such as the smoothing step of the method disclosed in U.S. Pat. No. 4,811,632, the tolerances are set by the raising of the margin and are significantly smaller than with the cutting edges disclosed in U.S. Pat. No. 4,811,632.

By the method of the invention, each of the cutting edges 62 are curved generally in the direction of the surfaces of the cup-blank 48 with a radius or minor axis of a non-circular arch shorter than the radius or minor axis of the cup-blank 48 as determined by the curvature of the margin 54 prior to deformation. In a specific embodiment of the invention the height of the cutting edges 64 from the outside surface of the acetabular reamer cup 10 is the same within a selected tolerance. In that embodiment, the tolerance is about plus or minus 0.005 inches.

Comparing the acetabular reamer cup 10 of the invention with prior acetabular reamer cups, a cavity can be formed in a pelvic bone with smaller tolerances than heretofore possible because of the greater consistency between cutting edges 64. With the acetabular reamer cup 10 of the invention, plus or minus 0.005 inches tolerances can be relatively achieved whereas heretofore normal tolerances were plus or minus 0.010 inches. Such tolerances are desired with a new "cementless" hip joints.

Additionally the improved sharpness of the cutting edges 64 can be documented by comparison testing using the following:

TESTING EQUIPMENT

Pattern mahogany in squares approximately 2.75" with a 0.500" pilot hole.

Enco milling and drilling machine Model No. 91034.

The tester is belted to operate at 300 RPM's.

May be purchased from: Enco Manufacturing Co. Chicago, Ill.

Dial indicator with a travel from 0.001"–1.00"

A timer such as a West Bend electronic timer, Cat. No. 4000.

May be purchased from: The West Bend Company, West Bend, Wis. 53095.

TESTING PROCEDURE

Select a shaft assembly 14 that best fits the cup needing testing.

Placing cup on selected shaft assembly 14, use a locking pin and secure cup to the shaft assembly 14.

Select proper mahogany block for test. If testing a 40–45 MM cup, use a new block with a pilot hole. If testing a 46 MM or larger cup, a block may be reused. For example if a mahogany block has been used to test a 54 MM cup, it can be used to test a 56 MM cup, etc. In all cups the entire spherical cutting path will be tested.

Place the mahogany block in the vise located at the base of the sharpness tester, and tighten the vise until the mahogany block is firm in place. Lowering he shaft assembly 14 down on the top of he block, center the top of he cup to the pilot hole by moving the adjustment handles left, right, back or forward.

Using the adjustment arm to move the base up and down, set the dial on zero.

Set the timer for a period of 5 seconds for any cup 50 MM or smaller; 7 seconds for 51 MM to 59 MM, and 10 seconds for grater cups 60 MM and up.

Set the timer according to the cup size and start your tester by turning the switch to the ON position. The switch is located on the top left-hand side of the tester. Turn the switch to the OFF position when the time has expired.

Refer to the dial indicator for depth of cut.

A minimum cut of 0.350" shall be acceptable.

Prior art cutting edges and edges 64 are compared in the following table:

| Rim Size | Time Of Cut | Prior Art | Cutting Edges 42 |
| --- | --- | --- | --- |
| 42 | 7 seconds | .460" | .920" |
| 44 | 7 seconds | .405" | .810" |
|  | 5 seconds | .359" | .718" |
| 48 | 5 seconds | .150" | .299" |
| 56 | 7 seconds | .045" | .091" |
| 58/57 | 7 seconds | .145" | .292" |

In a specific embodiment of the invention, cuttings edges 64 are each raised from a substantial part, but less than the entire cutting portion specific embodiment of the invention, cutting edges 64 extend out 108° to about 192° around the openings 28. In a specific embodiment of the invention of which the openings 28 are arranged in the pattern which forms a spiral upon rotation upon the acetabular reamer cup 10 about its axis 24, cutting edges 64 are arranged on margins 54 of the openings 28 to cut the spiral pattern defined by rotation of the acetabular reamer cup 10 about its axis 24. In other specific embodiments, the cutting edges 62, can be arranged on margins 54 to cut in other directions, for example, the direction of rotation of the acetabular reamer cup 10.

The acetabular reamer cup 10 produced by the method of the invention is used by connecting it to the shaft of a tool driver such as disclosed in U.S. Pat. No. 5,236,435 and connecting the shaft to a power drill the acetabular reamer cup 10 is pressed against the pelvis of a patient while it is rotating and a cavity is cut for the implantation of an artificial joint.

While a specific embodiment of the invention has been shown and described herein for purposes of illustration, the protection afforded by any patent which may issue upon this application is not strictly limited to the disclosed embodiment; but rather extends to all structures and arrangements which fall fairly within the scope of the claims which are appended hereto:

What is claimed is:

1. An acetabular reamer cup comprising a cutting bowl having a plurality of curved cutting edges, said cutting bowl having a plurality of openings preceding said cutting edges, said cutting bowl having a generally conical rise following said cutting edges, said conical rise having an apex angle generally from about 8° to about 46°, said cutting edges being spirally arranged about the axis of rotation of said cutting bowl.

2. The acetabular reamer cup of claim 1 wherein each of said cutting edges have a curvature in the same direction as said cutting bowl and are disposed to cut upon rotation of said acetabular reamer cup.

3. The acetabular reamer cup of claim 2 wherein said curvature of said cutting edges has a shorter radius than said bowl.

4. The acetabular reamer cup of claim 1 wherein each of said cutting edges have a curvature about the radius of said bowl, the radius of said curvature being smaller than the radius of said bowl.

5. The acetabular reamer cup of claim 1 wherein each of said cutting edges has an exterior surface and a beveled tapered portion intersecting said exterior surface of said cutting edge, said tapered portion being interior of said cutting bowl.

6. The acetabular reamer cup of claim 1 wherein said opening preceding said cutting edges is oval with a larger radius end and a smaller radius end, said larger radius end of said opening being remote from said cutting edge.

7. The acetabular reamer cup of claim 1 wherein said cutting edges upon rotation of said cutting bowl about said axis of rotation, each sweep an area overlapped by adjacent cutting edges a total of about 1½ times.

8. The acetabular reamer cup of claim 1 wherein said conical rise has an apex and a plane perpendicular to the exterior surface of said cutting bowl being from about 13° to about 23°, and an apex angle and a plane generally tangential to said exterior surface from about 8° to about 18°.

9. The acetabular reamer cup of claim 1 wherein said conical rise is generally oval in cross-section.

10. The acetabular reamer cup of claim 1 further comprising a bottom adjoined to said cutting bowl, wherein said bottom having an opening therein providing access to the interior of said bowl to remove cutting debris as desired said bottom opening being coaxial with said cutting bowl.

11. The acetabular reamer cup of claim 1 further comprising a tool driver connector mounted within said bottom opening.

12. The acetabular reamer cup of claim 11 wherein said tool driver connector is a pair of diametrically opposite peripheral openings in said cutting bowl.

13. The acetabular reamer cup of claim 11 wherein said tool driver connector is a diametral bar extending across said bottom opening, said diametral bar having a centering device midway between the opposite ends of said diametral bar.

14. The acetabular reamer cup of claim 13 wherein said centering device is a pin opening.

15. The acetabular reamer cup of claim 13 wherein said centering device is an enlargement an equal distance between the opposite ends of said bar, said enlargement having a shape which is complementary to an opening in a tool driver in which the cutting bowl is to be attached.

16. The acetabular reamer cup of claim 15 wherein said enlargement is a disc.

* * * * *

UNITED STATES PATENT AND TRADEMARK OFFICE
CERTIFICATE OF CORRECTION

| | |
|---|---|
| PATENT NO. | : 6,428,543 B1 |
| APPLICATION NO. | : 09/374034 |
| DATED | : August 6, 2002 |
| INVENTOR(S) | : Salyer |

It is certified that error appears in the above-identified patent and that said Letters Patent is hereby corrected as shown below:

Column 3

Line 62 delete "horizontal" and substitute --hemispherical-- therefor.

Column 7

Line 1, after "portion" insert --58.-- therefor; and
Line 1, before "specific" insert --In a-- therefor.

Signed and Sealed this

Fifth Day of June, 2007

JON W. DUDAS
*Director of the United States Patent and Trademark Office*